US011865024B2

United States Patent
Gomez et al.

(10) Patent No.: US 11,865,024 B2
(45) Date of Patent: *Jan. 9, 2024

(54) SUPPORT BRACE (71) Applicant: DJO, LLC, Carlsbad, CA (US)

(72) Inventors: Nicholas Gomez, Carlsbad, CA (US); Ian Kovacevich, Carlsbad, CA (US); Richard E Gildersleeve, Carlsbad, CA (US); John Patrick Martin, Vista, CA (US); David Orr, Vista, CA (US)

(73) Assignee: DJO, LLC, Carlsbad, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/883,934

(22) Filed: Aug. 9, 2022

(65) Prior Publication Data
US 2023/0201017 A1 Jun. 29, 2023

Related U.S. Application Data (63) Continuation of application No. 15/216,606, filed on Jul. 21, 2016, now Pat. No. 11,413,179, which is a
(Continued)

(51) Int. Cl.
A61F 5/00 (2006.01)
A61F 5/01 (2006.01)
A61F 5/30 (2006.01)

(52) U.S. Cl.
CPC ............. A61F 5/0109 (2013.01); A61F 5/30 (2013.01); A61F 2005/0181 (2013.01)

(58) Field of Classification Search
CPC ........... A61F 2005/0181; A61F 5/0111; A61F 5/0118; A61F 5/024; A61F 5/028;
(Continued)

(56) References Cited

U.S. PATENT DOCUMENTS 2,641,761 A * 6/1953 Schultz ............... A41D 13/065
602/26
3,934,583 A 1/1976 Hollingshead et al.
(Continued)

FOREIGN PATENT DOCUMENTS

CN 103079501 A 5/2013
DE 29803103 U1 5/1998
(Continued)

OTHER PUBLICATIONS

International Search Report and Written Opinion dated Apr. 8, 2015 on related application PCT/US2015/014256 filed Feb. 3, 2015.

Primary Examiner — Adam Baker
(74) Attorney, Agent, or Firm — Veros Legal Solutions, LLP (57) ABSTRACT Support braces and methods of manufacturing the same are disclosed. A support brace includes a flexible fabric substrate and an elastomeric member disposed on the surface of the flexible fabric substrate. The elastomeric member is disposed so as to apply pressure non-uniformly about a limb or joint of the wearer, in a pattern selected to divert pain and/or reduce loads on the joint. The flexible fabric substrate can include regions having different levels of elasticity, to provide different levels of compression to different parts of the joint or limb in addition to the compression provided by the elastomeric member. The elastomeric member can be deposited, screen printed, injection molded, or otherwise applied to the fabric substrate, optionally without adhesive.

20 Claims, 7 Drawing Sheets

Related U.S. Application Data continuation of application No. PCT/US2015/014256, filed on Feb. 3, 2015.

(60) Provisional application No. 61/935,296, filed on Feb. 3, 2014.

(58) Field of Classification Search
CPC .......... A61F 5/30; A61F 5/373; A61F 13/061; A61F 13/062; A61F 13/08; A61F 13/085; A63B 2071/125
USPC .............................................. 602/26, 23, 24
See application file for complete search history.

(56) References Cited

U.S. PATENT DOCUMENTS

| | | |
|---|---|---|
| 4,700,698 A | 10/1987 | Kleylein |
| 5,823,981 A | 10/1998 | Grim et al. |
| 6,077,242 A | 6/2000 | Falk et al. |
| 6,149,616 A | 11/2000 | Szlema et al. |
| 7,004,919 B2 | 2/2006 | Gaylord et al. |
| 7,959,590 B2 | 6/2011 | Scott |
| 2004/0134501 A1 | 7/2004 | Hargis et al. |
| 2005/0020951 A1 | 1/2005 | Gaylord et al. |
| 2006/0026736 A1 | 2/2006 | Nordt et al. |
| 2006/0041214 A1 | 2/2006 | Reinhardt et al. |
| 2007/0167891 A1 | 7/2007 | Gramza et al. |
| 2008/0139985 A1 | 6/2008 | Gilmour |
| 2010/0056973 A1 | 3/2010 | Farrow et al. |

FOREIGN PATENT DOCUMENTS

| | | |
|---|---|---|
| EP | 1629811 A1 | 3/2006 |
| WO | 1985004569 A1 | 10/1985 |

* cited by examiner

SUPPORT BRACE

CROSS-REFERENCE TO RELATED APPLICATIONS

This application is a continuation of and claims priority to U.S. application Ser. No. 15/216,606, filed on Jul. 21, 2016 and will issue as U.S. Pat. No. 11,413,179 on Aug. 16, 2022, which is a continuation of and claims priority to PCT Application PCT/US2015/014256 filed on Feb. 3, 2015, which claims priority to U.S. Provisional Application No. 61/935,296, filed on Feb. 3, 2014, the disclosures of which are hereby incorporated by reference in their entireties.

BACKGROUND OF THE INVENTION

Field of the Invention

This application relates to devices for supporting a joint or limb. More particularly, this application relates to wearable braces for reducing joint or limb pain and for improving joint or limb function.

Description of the Related Technology

Osteoarthritis (OA), commonly known as wear-and-tear arthritis, is a condition in which the natural cushioning between joints wears away. Osteoarthritis is one of the most frequent causes of physical disability among adults, with over 20 million people in the United States having the disease. A degenerative joint disease, osteoarthritis causes chronic pain in the affected joint when the joint is statically or dynamically loaded.

Primary osteoarthritis often affects weight bearing joints, such as the knee. Repetitive use of a joint, such as the knee, over time can irritate and inflame the cartilage, causing joint pain and swelling. Eventually, cartilage begins to degenerate and as cartilage is diminished, the bones of the knee joints rub more closely against one another with less of the shock-absorbing benefits of cartilage. The rubbing can result in pain, swelling, stiffness, decreased mobility as well as the possibility of bone spur formation. The most common cause of osteoarthritis of the knee is age. However, several factors increase the risk of developing significant arthritis including age, weight, repetitive stress injuries, and certain athletic endeavors such as soccer, tennis, or long-distance running.

In an affected knee, osteoarthritis pain is often caused by an unbalanced loading on the medial or lateral compartment of the joint. Such unbalanced loading can generate increased pressure and reduce the clearance space between the condyles of the femur and tibial plateau. Increased pressure between the femoral and tibial surfaces in an affected compartment of the knee joint can lead to cartilage degeneration. As the cartilage degenerates, the osteoarthritis sufferer experiences increased pain in the knee.

Orthopedic knee braces are commonly applied to the leg to treat osteoarthritis of the knee and other painful knee conditions. Such braces typically include an upper support portion, a lower support portion, and one or more hinge assemblies pivotally interconnecting the upper and lower support portions. The upper support portion is secured to the wearer's upper leg, while the lower support portion is secured to the wearer's lower leg. The hinge assembly (or assemblies) is located to a side of the wearer's knee and a condyle pad is typically located between each hinge assembly and the adjacent side of the knee.

Knee braces are available which utilize a single upright support attached to an upper thigh cuff and lower shin cuff. The upright support is located opposite to or adjacent to the side of the collapsed compartment of the knee. The attached cuffs "unload" the biomechanical force on the affected compartment of the knee by increasing the joint space on the affected side as the knee goes from flexion to extension. Other known brace designs employ a double upright strut, which immobilizes the knee by unloading the degenerative knee compartment. In some prior art devices, non-slippage and comfort pads are employed along inner lateral surfaces of the upright struts.

Patients who suffer joint pain may also benefit from the use of compression sleeves or wrap-arounds. Available compression sleeves use a flexible, elastic fabric, such as neoprene, designed to be pulled over or wrapped around the joint. Compression sleeves can improve joint stability and also provide some insulation or heat to the joint. In some instances, a compression sleeve may include one or more rods which may provide support to the joint.

SUMMARY

In a first aspect, a knee brace includes a flexible fabric substrate configured to encircle the knee of a wearer and to extend above and below the wearer's knee, and a first elastomeric member disposed on a first surface of the flexible fabric substrate. The elastomeric member is configured to reduce loads on the knee joint. The first elastomeric member can be configured to apply pressure non-uniformly about the wearer's patella. The first elastomeric member can be disposed on the first surface of the flexible fabric substrate so as to extend through an arc of between about 180 and 320 degrees about the wearer's patella. At least a portion of the first elastomeric member can extend laterally of the wearer's patella. The knee brace can also include a second elastomeric member disposed on the first surface of the flexible fabric substrate, the second elastomeric member being spaced apart from the first elastomeric member and disposed medially of the wearer's patella. The knee brace can also include a third elastomeric member disposed on a second surface of the flexible fabric substrate; the second surface facing an opposition direction from the first surface. The third elastomeric member can have a dimpled surface. The first elastomeric member can comprise silicone. The first elastomeric member can have a thickness of between about 0.5 mm and about 5 mm. The flexible fabric substrate can comprise a generally tubular sleeve. The flexible fabric substrate can comprise a wrap-around. The flexible fabric substrate can comprise at least a first region and a second region, the second region having a higher modulus of elasticity than the first region. The first elastomeric member can be joined to the flexible fabric substrate with or without adhesive.

In a second aspect, a method of manufacturing a knee brace includes providing a flexible fabric substrate configured to encircle the knee of a wearer and to extend above and below the wearer's knee and applying a first elastomeric member to a first surface of the flexible fabric substrate in a pattern selected to reduce loads on the knee joint. The first elastomeric member can be applied by an injection molding process. The first elastomeric member can be applied to a thickness of between about 0.5 mm and about 5 mm. The first elastomeric member can be applied to the first surface of the flexible fabric substrate so as to extend through an arc of between about 180 and 320 degrees about the wearer's patella. The method can further include applying a second elastomeric member to the first surface of the flexible fabric substrate, the second elastomeric member being spaced apart from the first elastomeric member such that the second elastomeric member is disposed medially of the wearer's patella.

BRIEF DESCRIPTION OF THE DRAWINGS

The above-mentioned and other features of the invention will now be described with reference to the drawings of certain embodiments which are intended to illustrate but not to limit the invention. The drawings contain the following figures.

DETAILED DESCRIPTION OF CERTAIN INVENTIVE EMBODIMENTS

Conventional braces provide support using bulky fabrics and hardware which are inconvenient for everyday wear. In contrast, embodiments of the invention provide a low-profile and lightweight brace which is easy to apply and wear, even under non-athletic clothing. Embodiments can generally include a fabric base layer, such as a knitted sleeve or wrap-around, having elastomeric material disposed thereon. The elastomeric material can be disposed non-uniformly about the joint, in a pattern selected to provide targeted force biases and/or compression in specific locations adapted to reduce loads on the joint and/or divert pain from problem areas. The elastomeric material can be configured to reinforce and/or complement any compression offered by the fabric base layer. By such a configuration, a brace can be provided which improves joint or limb function and reduces pain without the hardware or bulk of a conventional design. Embodiments can be used to advantage to reduce pain, prevent injury, and promote rehabilitation in any anatomical region of the body where compression can assist with these goals, such as, for example, the wrist, forearm, elbow, shoulder, torso, hip, knee, calf, or ankle.

Figure 1A:
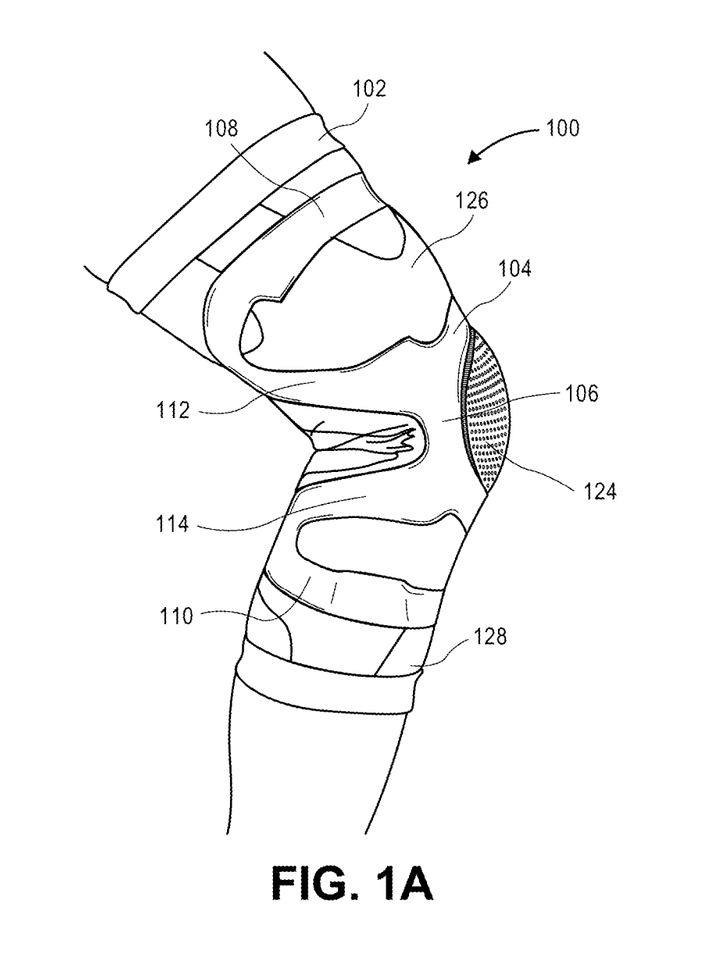
FIG. 1A is a lateral side perspective view of one example of a knee brace configured in accordance with an embodiment, shown on a wearer's right leg.

With reference now to FIG. 1A, one example of a knee brace 100 is illustrated. FIG. 1A shows a lateral side perspective view of the knee brace 100 on a wearer's right leg. The knee brace 100 includes a flexible fabric base or substrate 102 and an elastomeric member 104. As shown in FIG. 1A, the elastomeric member 104 includes a curvilinear portion 106 extending around the lateral side of the patella. As illustrated in FIG. 1A, the curvilinear portion 106 is continuous along the length of the knee joint on the lateral side of the patella. By such a configuration, the elastomeric member 104 can help to unload in the frontal plane a medial or lateral knee compartment, and/or resist extension of the knee on the lateral side. In some embodiments, the first elastomeric member 104 or portions thereof (e.g., the curvilinear portion 106) can extend through an arc of, for example, less than 180 degrees, greater than 180 degrees, less than 320 degrees, greater than 320 degrees, between about 180 and 320 degrees, between about 200 and 300 degrees, or between about 220 and 280 degrees around the wearer's patella, or within a range defined by any of these numbers. The elastomeric member 104 also includes a thigh portion 108 and a calf portion 110, which extend generally horizontally around the thigh and the calf, respectively. The thigh portion 108 and the calf portion 110 can be adapted to provide compression across the bone/tendon junctures above and below the knee joint. The elastomeric member 104 also includes a connecting portion 112, which extends upward and posterior from the curvilinear portion 106 to connect with a posterior end of the thigh portion 106, and a connecting portion 114, which extends downward and posterior from the curvilinear portion 106 to connect with a posterior end of the calf portion 110.

Figure 1B:
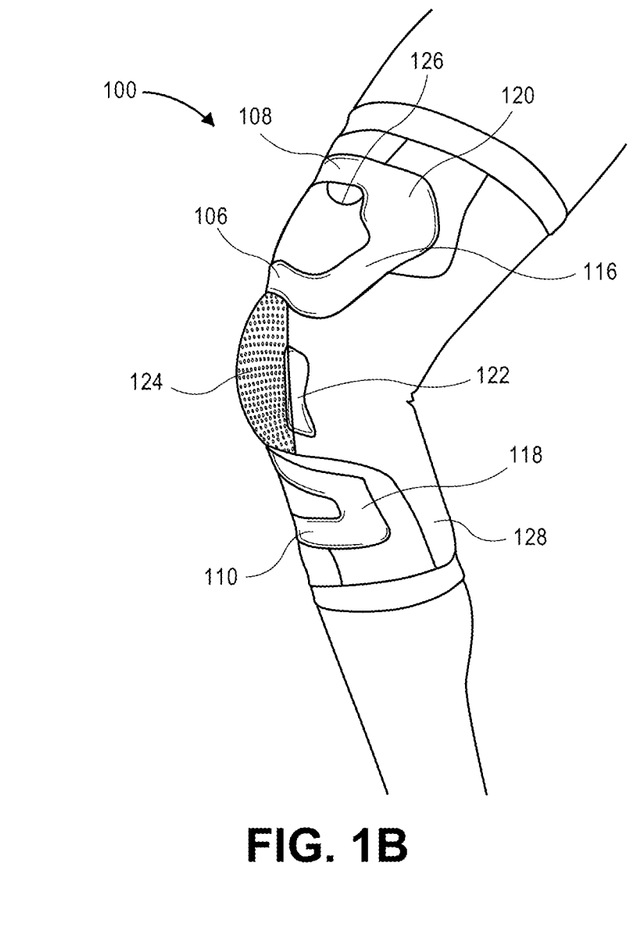
FIG. 1B is a medial side perspective view of the knee brace of FIG. 1A.

FIG. 1B is a medial side perspective view of the knee brace 100, and illustrates that the curvilinear portion 106 is discontinuous about the medial side of the patella. Such a discontinuity can facilitate or promote extension of the knee on the medial side. FIG. 1B also shows a connecting portion 116, which extends upward from the curvilinear portion 106 to connect with an anterior end of the thigh portion 108, and a connecting portion 118, which extends downward from the curvilinear portion 106 to connect with an anterior end of the calf portion 110. The elastomeric member 104 can include an enlarged portion 120 at or near the juncture of the connecting portion 116 with the thigh portion 108. The enlarged portion 120 may be disposed at or near the region of the vastus medialis oblique (VMO) muscle. In some embodiments, the brace 100 can include an additional elastomeric member 122 on the medial side of the patella, spaced apart from the elastomeric member 104.

The fabric base 102 can include a fabric, such as a knit or otherwise stretchy fabric, to provide compression around the joint. In some embodiments, the fabric base 102 can include a non-stretchy fabric. Alternatively or in addition, the fabric base 102 can include regions with one or more different degrees of stretchiness (e.g., different types of knit; different moduli of elasticity), allowing the brace 100 to provide different levels of compression to different anatomical regions about the joint. For example, as illustrated in FIGS. 1A and 1B, the fabric base 102 can include a first region 124 having a relatively low elastic modulus, for example in the region of the patella, to allow freedom of movement of the patella and avoid unwanted compression of the patella against the other structures of the knee joint. The fabric base 102 can also include a second region 126 having a relatively higher level of compression, for example in the region immediately above and below the patella. The fabric base can also include a third region 128 having a third and even higher level of compression, for example in the regions encircling the thigh and the calf.

Figure 2A:
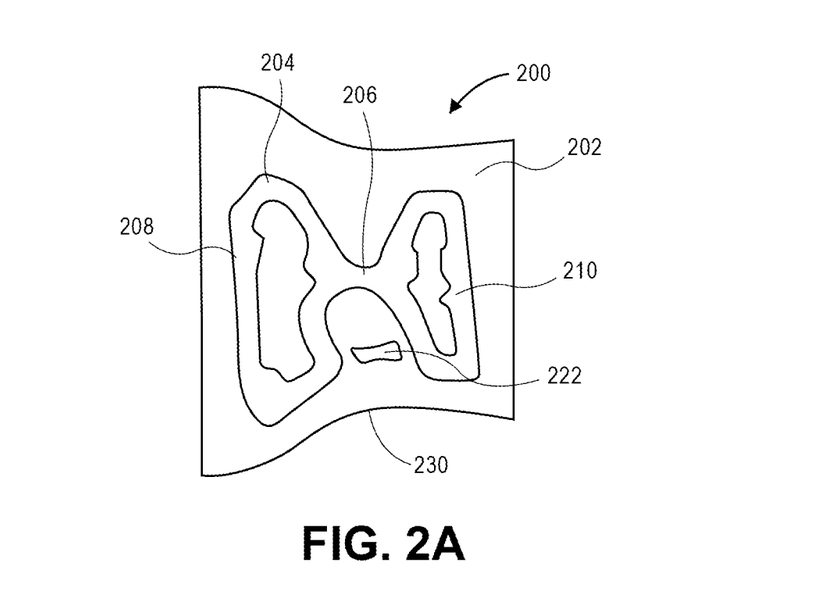
FIG. 2A is a plan view of the outer surface of another example of a knee brace, adapted to be worn on the left leg, shown cut open along a seam and laid flat, with certain detail omitted to better illustrate the elastomeric member.

FIG. 2A is a plan view of the outer surface of a left knee brace 200 having all the same features as the right brace 100, in which like reference numbers reflect like parts. In FIG. 2A, the details of the regions of varying compression are omitted to better illustrate the configuration of the elastomeric members 204 and 222, including, for example, the curvilinear portion 206, the thigh portion 208, and the calf portion 210 of the member 204. In FIG. 2A, the brace 200 is cut open along a seam 230 and laid flat.

Figure 2B:
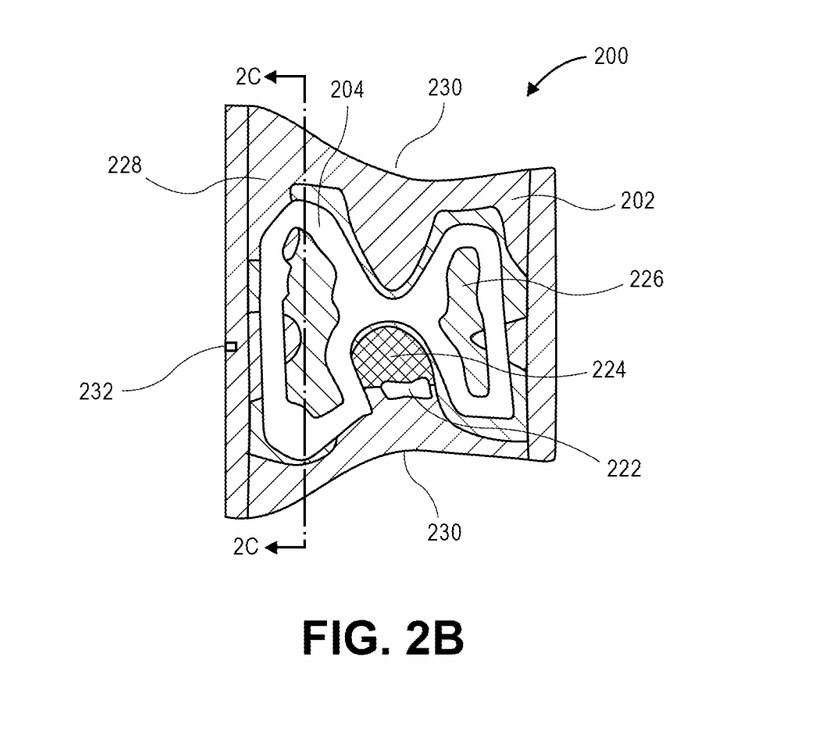
FIG. 2B is a plan view of the outer surface of the knee brace of FIG. 2A, shown cut open along a seam and laid flat, illustrating additional details that the base layer can include.

FIG. 2B is a plan view of the outer surface of the knee brace 200, also cut open along the seam 230 and laid flat, with the details of the first region 224 (having a first and lower level of compression), second region 226 (having a second and higher level of compression), and third regions 228 (having a middle level of compression, between that of the first and second regions 224, 226). Also illustrated in FIG. 2C is a marker 232, which indicates the front midline of the brace, directly above the patella, which can be used by a wearer to assist in proper positioning of the brace 200.

Figure 2C:
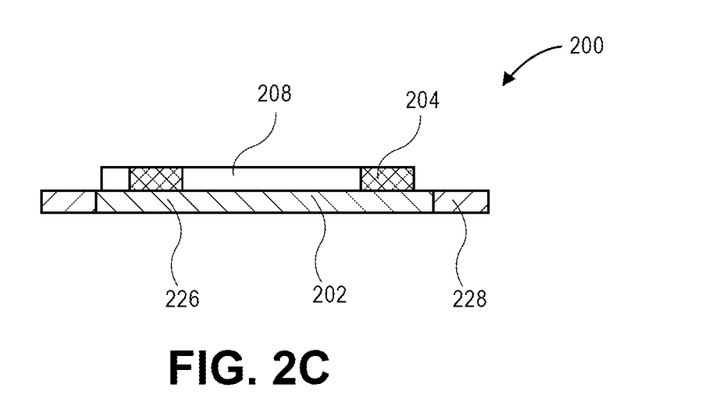
FIG. 2C is a cross-sectional view of the knee brace of FIG. 2B, taken along line 2C-2C.
Figure 2D:
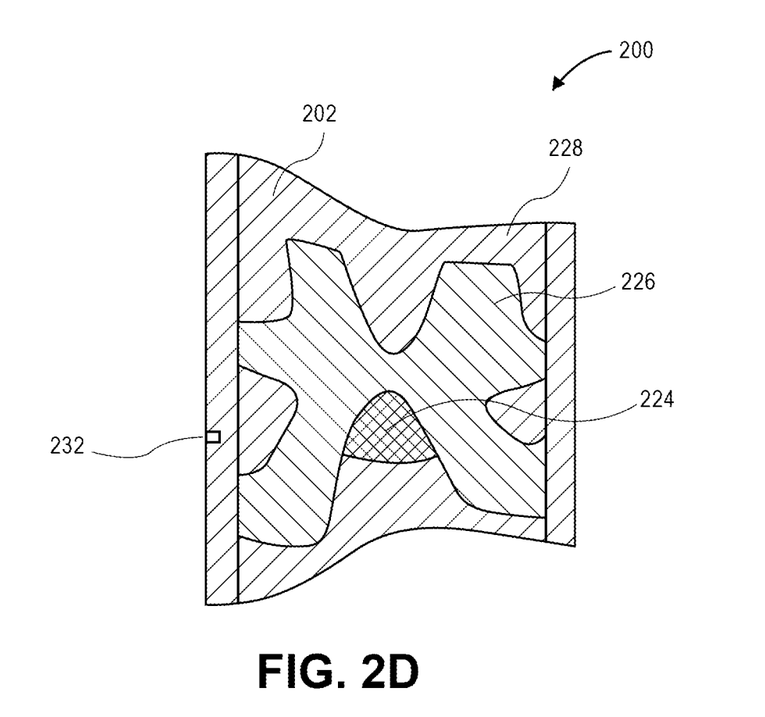
FIG. 2D is another plan view of the knee brace of FIG. 2B, shown with the elastomeric material removed to better illustrate the configuration of the base layer.

FIG. 2C is a cross-sectional view of the knee brace 200, taken along line 2C-2C of FIG. 2B. FIG. 2C shows the elastomeric member 204 disposed on outer surface of the fabric substrate 202. The section 2C-2C cuts through the second region 226 and the third region 228. FIG. 2D is another plan view of the knee brace 200, shown with the elastomeric material 204 removed to better illustrate the configuration of the first region 224, the second region 226, and the third region 228.

Figure 2E:
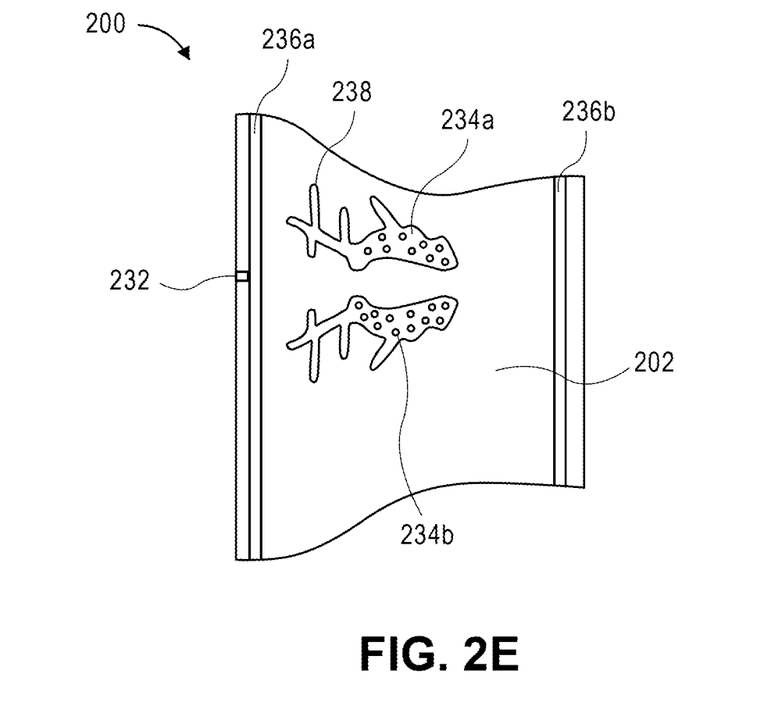
FIG. 2E is a plan view of the inner surface of the knee brace of FIG. 2A, shown cut open and laid flat, with the details of the regions of varying compression omitted.

FIG. 2E is a plan view of the inner surface of the knee brace 200, shown cut open and laid flat, with the details of the regions of varying compression omitted. In some embodiments, as illustrated in FIG. 2E, the knee brace 200 can include on its inner surface one or more elastomeric members 234a, 234b. In the embodiment illustrated in FIG. 2E, the elastomeric members 234a, 234b are disposed on either side of the patellar region, and are configured as mirror images of one another. The elastomeric members 234a, 234b can be disposed so as to assist the wearer in properly positioning the brace 200, and also to facilitate proper patellar tracking. The elastomeric members 234a, 234b can have a tacky surface, to help the brace 200 stay in place on the skin when worn. As illustrated in FIG. 2E, in some embodiments, the elastomeric members 234a, 234b can include one or more horizontally-extending bars 238 to reduce the risk of migration of the brace 200 during wear. In some embodiments, the elastomeric members 234a, 234b can have a dimpled, striated, or otherwise textured surface, which can assist in proprioception. The knee brace can also include one or more elastomeric members 236a, 236b disposed, respectively, so as to at least partly encircle the thigh and calf. The elastomeric members 236a, 236b can also have a tacky surface to help the brace stay in place on the skin when worn.

The knee braces 100 and 200 illustrated, respectively, in FIGS. 1 and 2A-2E, and other embodiments incorporating one or more features discussed herein can be used to help reduce pain, prevent injury, and promote rehabilitation in patients suffering from meniscus and/or cartilage damage, anterior knee pain, tendonitis, osteoarthritis or early stage osteoarthritis of the knee joint and knee cap.

The provision of one or more elastomeric members on a surface of a flexible fabric substrate in a support brace can serve to strategically reinforce or add to any compression provided by the substrate itself, in a specific design targeted to support certain joint or limb structures, facilitate or resist specific movements of the joint, and/or subtly off-load certain joint structures (e.g., to increase the space between certain structures in the joint). For example, in a knee brace according to an embodiment, one or more elastomeric members can be oriented in three points of leverage in the frontal plane, so as to reduce loads on the medial and/or lateral compartments of the knee joint. Additionally or alternatively, one or more elastomeric members can include one or more circumferential bands either partly or completely surrounding the joint or limb (e.g., extending about or more than halfway around the joint or limb), proximal and/or distal of the joint. Such circumferential bands can act as alternative termination points at the muscle/tendon juncture, thereby reducing forces on the joint. Additionally or alternatively, one or more elastomeric members can include bars or other longitudinally-extending sections crossing the joint and positioned so as to assist or resist extension or flexion in desired anatomical locations. For example, in one embodiment comprising a knee brace, longitudinally-extending bars can be provided on the anterior side of the knee and configured to assist extension and resist flexion of the knee, thus easing ambulation efforts. In another embodiment comprising a knee brace, one or more elastomeric members can be disposed so as to laterally support the patella and thereby resist patellar subluxation.

Figure 3:
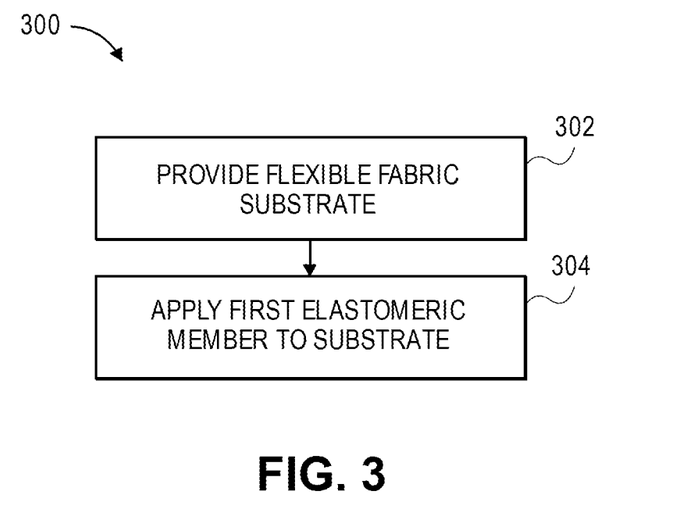
FIG. 3 is a block diagram illustrating a method for manufacturing a knee brace, in accordance with an embodiment.

With reference now to FIG. 3, a process 300 for manufacturing a support brace is illustrated. At a block 302, a flexible fabric substrate or base layer is provided. In some embodiments, the base layer can comprise a comfortable, stretchable, and breathable material, such as a fabric made with circular or flat knitting. The base layer can be adapted to provide both compression and warmth to the joint or limb when worn. The base layer can comprise, for example, a blend of bamboo fiber (e.g. carbonized bamboo), cotton, nylon, polyester, polypropylene, wool, and/or spandex. The base layer can be configured with a 2-way stretch or a 4-way stretch. The base layer can be provided with regions of differing levels of compression in any suitable fashion, for example by forming certain regions with a different type of fabric, a different type of knitting, or both. Further, the base layer can be provided with any suitable overall form to fit the joint or limb for which the brace is designed. For example, in some embodiments, such as an embodiment adapted for a knee, calf, forearm, or elbow, the base layer can have the form of a tubular sleeve, or a wrap-around configured to closely surround the joint or limb (e.g., with hook-and-loop fasteners, laces, hooks, zippers, or other types of closures, optionally allowing an adjustable fit). In some embodiments, the base layer can be produced as an uninterrupted tube, which is cut and laid open to facilitate deposition of an elastomeric material thereon, and then stitched or otherwise joined back together before being provided to the wearer.

At a block 304, a first elastomeric member can be applied to a surface of the flexible fabric substrate. The elastomeric member can be applied to an outer surface or an inner surface of the substrate. The elastomeric member can be any suitable elastomer, such as, for example, polyurethane, polyvinyl chloride, SANTOPRENE® thermoplastic vulcanizate, silicone, or any other suitable thermoset or thermoplastic elastomer or combination of elastomers. The elastomer can be applied to the substrate in any suitable manner, for example using an adhesive (e.g., a pressure-sensitive adhesive), melting, stitching, depositing, injection molding, printing (e.g., silk screening), welding, being cast in place, or any other method adapted to securely bond the elastomer to the substrate. In one example of a welding process, the elastomer can be cast into the desired shape and thickness, separately from the base layer, and can then be welded onto the base layer. In one example of a printing process, an elastomer such as silicone can be applied through a screen and mask in a desired shape and then allowed to set for a suitable time to release any trapped air bubbles. The elastomer can then be reapplied, perhaps multiple times, until the desired thickness is achieved. In another example of a printing process, an elastomer can be applied into a form or stencil having the desired shape, allowed to set, and then reapplied (if necessary) to the desired thickness. In some embodiments, the elastomer can be applied to the substrate by injection molding. In such an embodiment, the elastomer can be applied with a constant thickness, or alternatively in varying thicknesses, optionally in a single processing step. Any regions of varying thickness can be gently graduated or sharply delineated. In embodiments, the application technique and type of elastomer can preferably be resistant to delamination or other degradation due to wear and tear (e.g. washing and drying, exposure to sweat, sunscreen, and dirt).

The elastomeric member(s) can have any suitable thickness. For example, the elastomeric member(s) disposed on the outer surface of the base layer can have a thickness ranging between about 0.3 mm to 5 mm, or between about 0.5 mm to 5 mm. Also for example, the elastomeric member(s) disposed on the inner surface of the base layer can have a thickness ranging between about 0.3 mm to 3 mm, or between about 0.5 mm to 3 mm. As mentioned above, the thickness of the elastomeric member(s) can be uniform across each elastomeric member, or can be variable throughout the pattern of each elastomeric member. For example, in a knee brace, an elastomeric member disposed on the outer surface of the base layer can be thicker in a region where additional compression is desired, such as in the regions crossing the thigh and/or calf, and can be thinner in a region where more flexibility is desired, such as in the region where the knee bends. The elastomeric member(s) can be disposed in any suitable pattern adapted to support the joint or limb and minimize discomfort associated with any target pain condition (i.e., osteoarthritis, anterior knee pain, patellofemoral pain, or another joint pain condition of the knee or any other joint or anatomical region of the body).

Figure 4:
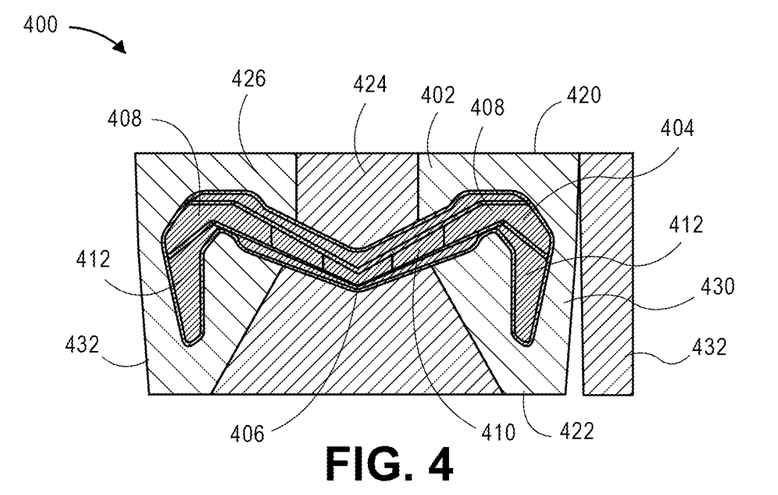
FIG. 4 is a plan view of the outer surface of another example of a support brace configured in accordance with an embodiment, being adapted to be worn on the forearm, and shown cut open along two seams and laid flat.

FIG. 4 is a plan view of the outer surface of another example of a support brace 400 configured in accordance with an embodiment, being adapted to be worn on the forearm, shown cut open along two seams 430, 432 and laid flat. In some embodiments, the brace 400 can be adapted to help alleviate pain from, for example, golfer's elbow or tennis elbow. The brace 400 includes a flexible fabric base 402 having a proximal region 420 adapted to be positioned near the wearer's elbow and a distal region 422 adapted to be positioned closer to the wearer's hand. The brace 400 also includes an elastomeric member 404 with a focal portion 406. The focal portion 406 can have a V-shaped configuration, as shown in FIG. 4, or a curved shape, with the apex of the V shape or curve configured to be placed at the site of pain and apply pressure thereto. For example, in the case of golfer's elbow, the focal portion 406 can be placed at the inside of the forearm, and in the case of tennis elbow, the focal portion 406 can be placed at the outside of the forearm. The elastomeric member can also include one or more wing portions 408 extending away from the focal portion 406, in such a way as to divert pain away from the focal region 406. In some embodiments, as illustrated in FIG. 4, the wing portions 408 can include both proximally-extending portions 410 (extending, for example, in generally the same direction as the legs of the V-shape) as well as distally-extending portions 412. The elastomeric member 404 can be configured to provide differential pressure at different positions around the forearm and divert pressure from the site of pain. In some embodiments, the elastomeric member 404 can include regions of varying thickness, to provide even more variability of compression at different locations around the forearm.

In some embodiments, the fabric base 402 can include regions with different degrees of stretchiness (e.g., different types of knit; different moduli of elasticity), also facilitating the provision of different levels of compression to different regions about the forearm. For example, as illustrated in FIG. 4, the fabric base 402 can include a first region 424 having a relatively low elastic modulus, and a second region 426 having a relatively higher level of compression.

Figure 5:
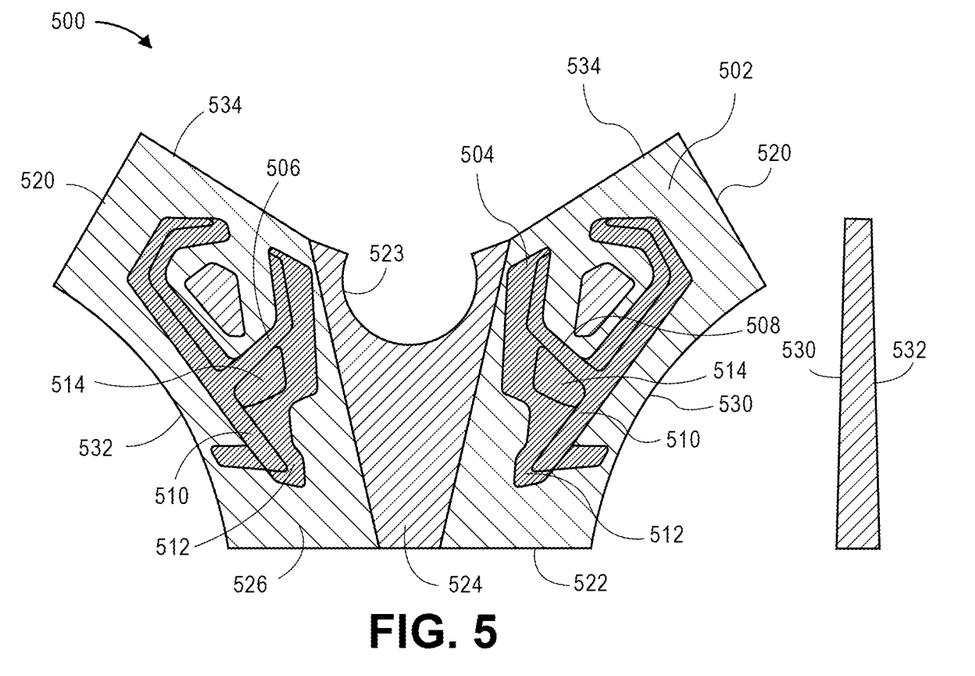
FIG. 5 is a plan view of the outer surface of another example of a support brace configured in accordance with an embodiment, being adapted to be worn on the ankle, and shown cut open along various seams and laid flat.

FIG. 5 is a plan view of the outer surface of another example of a support brace 500 configured in accordance with an embodiment, being adapted to be worn on the ankle, and shown cut open along various seams 530, 532, 534 and laid flat. In some embodiments, the brace 500 can be adapted to support a sprained or injured ankle. In some embodiments, the brace 500 can be adapted to inhibit or resist inversion and/or eversion of the foot. The brace 500 includes a flexible fabric base 502 having a proximal region 520 adapted to be positioned around the wearer's lower calf, a distal region 522 adapted to encircle the wearer's forefoot and/or midfoot, and a heel region 523 adapted to encircle the wearer's heel. The brace 500 also includes an elastomeric member 504, which can comprise a lateral portion 506 and a medial portion 508. The lateral and medial portions 506, 508 can be mirror images of one another, as shown in FIG. 5, or can be configured differently from one another. Further, the lateral and medial portions 506, 508 can be separate from one another, as shown in FIG. 5, or can be continuous with or otherwise connected to one another. In the embodiment illustrated in FIG. 5, the elastomeric member 504 comprises two support members 510 configured to extend along the upper part of the wearer's foot, generally between the forefoot and/or midfoot and the ankle. As shown in FIG. 5, each of the support members 510 includes a generally V-shaped portion, with the apex 512 of the V shape being disposed near the forefoot and the legs of the V shape extending back toward the heel and up toward the top of the ankle when the support 500 is worn. The apex 512 can include a filled in, webbed, or otherwise reinforced portion 514. The elastomeric member 504 can be configured to provide differential pressure at different positions around the foot and/or ankle and support the foot and ankle. In some embodiments, the elastomeric member 504 can include regions of varying thickness, to provide more or less compression at different locations around the foot and/or ankle, to allow for a better fit inside a shoe, and/or to interact with features in a shoe to provide or enhance stability.

In some embodiments, the fabric base 502 can include regions with different degrees of stretchiness (e.g., different types of knit; different moduli of elasticity), also facilitating the provision of different levels of compression to different regions about the foot and/or ankle. For example, as illustrated in FIG. 5, the fabric base 502 can include a first region 524 having a relatively low elastic modulus, and a second region 526 having a relatively higher level of compression.

Figure 6:
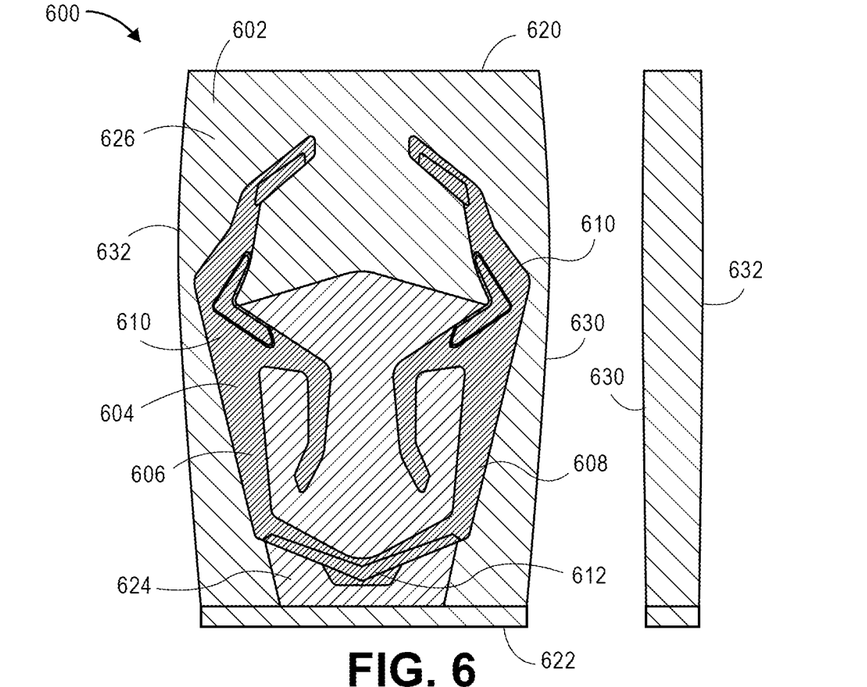
FIG. 6 is a plan view of the outer surface of another example of a support brace configured in accordance with an embodiment, being adapted to be worn on the calf, and shown cut open along two seams and laid flat.

FIG. 6 is a plan view of the outer surface of another example of a support brace 600 configured in accordance with an embodiment, being adapted to be worn on the calf, and shown cut open along two seams 630, 632 and laid flat. In some embodiments, the brace 600 can be adapted to support or divert pain in a strained or injured calf, for example, to divert pain from shin splints. The brace 600 includes a flexible fabric base 602 having a proximal region 620 adapted to be positioned around the wearer's upper calf, and a distal region 622 adapted to encircle the wearer's lower calf. The brace 600 also includes an elastomeric member 604, which can comprise a lateral portion 606 and a medial portion 608. The lateral and medial portions 606, 608 can be mirror images of one another, as shown in FIG. 6, or can be configured differently from one another. Further, the lateral and medial portions 606, 608 can be connected to one another, as shown in FIG. 6, or can be separate from one another. In the embodiment illustrated in FIG. 6, the lateral and medial portions 606, 608 each include a cradle portion 610 which cooperates with the other to cradle and support the calf muscle along the length of the calf and reduce shearing of muscle tissue. The elastomeric member 604 also includes a support member 612 which is configured to extend across and support the Achilles tendon when the brace 600 is worn. The elastomeric member 604 can be configured to provide differential pressure at different positions around the calf and support the structures of the calf and/or ankle, including, for example, the calf muscle and the Achilles tendon. In some embodiments, the elastomeric member 604 can include regions of varying thickness, to provide even more variability of compression at different locations around the calf and/or ankle. For example, thicker regions can be provided in the elastomeric member 704 to provide additional compression and support to maintain position of the brace when worn (e.g., to inhibit slippage of the brace down the leg or around the leg).

In some embodiments, the fabric base 602 can include regions with different degrees of stretchiness (e.g., different types of knit; different moduli of elasticity), also facilitating the provision of different levels of compression to different regions about the foot and/or ankle. For example, as illustrated in FIG. 6, the fabric base 602 can include a first region 624 having a relatively low elastic modulus, and a second region 626 having a relatively higher level of compression.

Figure 7:
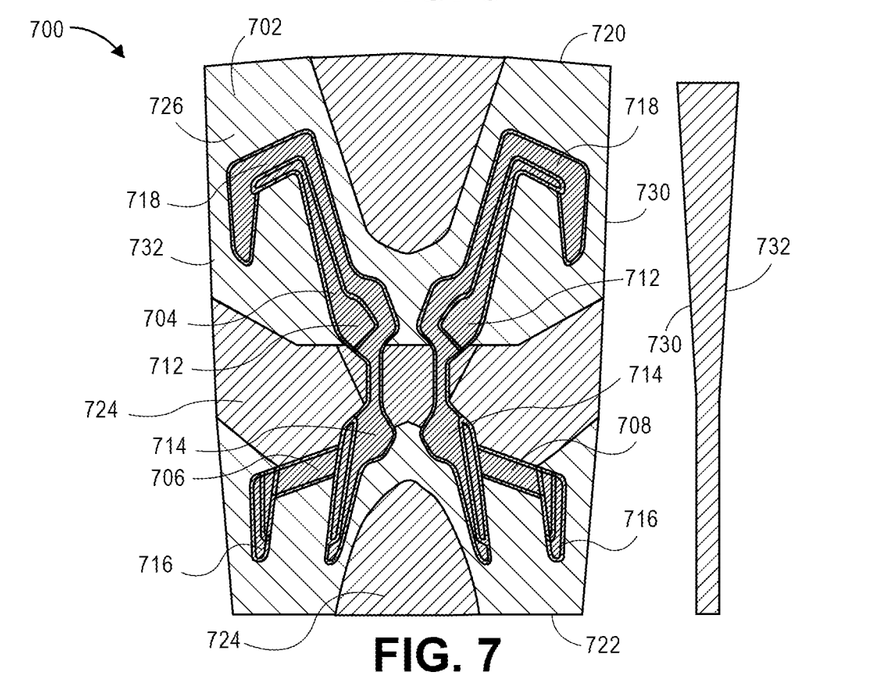
FIG. 7 is a plan view of the outer surface of another example of a support brace configured in accordance with an embodiment, being adapted to be worn on the elbow, and shown cut open along two seams and laid flat.

FIG. 7 is a plan view of the outer surface of another example of a support brace 700 configured in accordance with an embodiment, being adapted to be worn on the elbow, and shown cut open along two seams 730, 732 and laid flat. In some embodiments, the brace 700 can be adapted to support or divert pain in a strained or injured arm, for example, to divert pain from golfer's elbow or tennis elbow. The brace 700 includes a flexible fabric base 702 having a proximal region 720 adapted to be positioned around the wearer's upper arm, and a distal region 722 adapted to encircle the wearer's forearm. The brace 700 also includes an elastomeric member 704, which can comprise a first portion 706 and a second portion 708, each extending generally along the length of the wearer's arm. The first and second portions 706, 708 can be mirror images of one another, as shown in FIG. 7, or can be configured differently from one another. Further, the first and second portions 706, 708 can be separate from one another, as shown in FIG. 7, or can be connected to one another. In the embodiment illustrated in FIG. 7, the first and second portions 706, 708 can be configured to extend along opposite sides of the wearer's elbow so as to assist extension of the elbow joint and so as to provide shock absorption. The portions 706, 708 can each include one or more enlarged regions, such as regions 712, 714, which may be disposed proximal and/or distal of the elbow. The enlarged regions 712, 714 can be configured to apply additional pressure at pain points. The elastomeric member 704 can also include one or more wing portions 716, 718 extending away from one or more of the enlarged regions 712, 714 (or from other regions of the portions 706, 708), in such a way as to divert pain away from those regions. The elastomeric member 704 can be configured to provide differential pressure at different positions around the arm and support the structures of the arm and/or elbow. In some embodiments, the elastomeric member 704 can include regions of varying thickness, to provide even more variability of compression at different locations around the arm and/or elbow.

In some embodiments, the fabric base 702 can include regions with different degrees of stretchiness (e.g., different types of knit; different moduli of elasticity), also facilitating the provision of different levels of compression to different regions about the arm and/or elbow. For example, as illustrated in FIG. 7, the fabric base 702 can include a first region 724 having a relatively low elastic modulus, and a second region 726 having a relatively higher level of compression.

Figure 8:
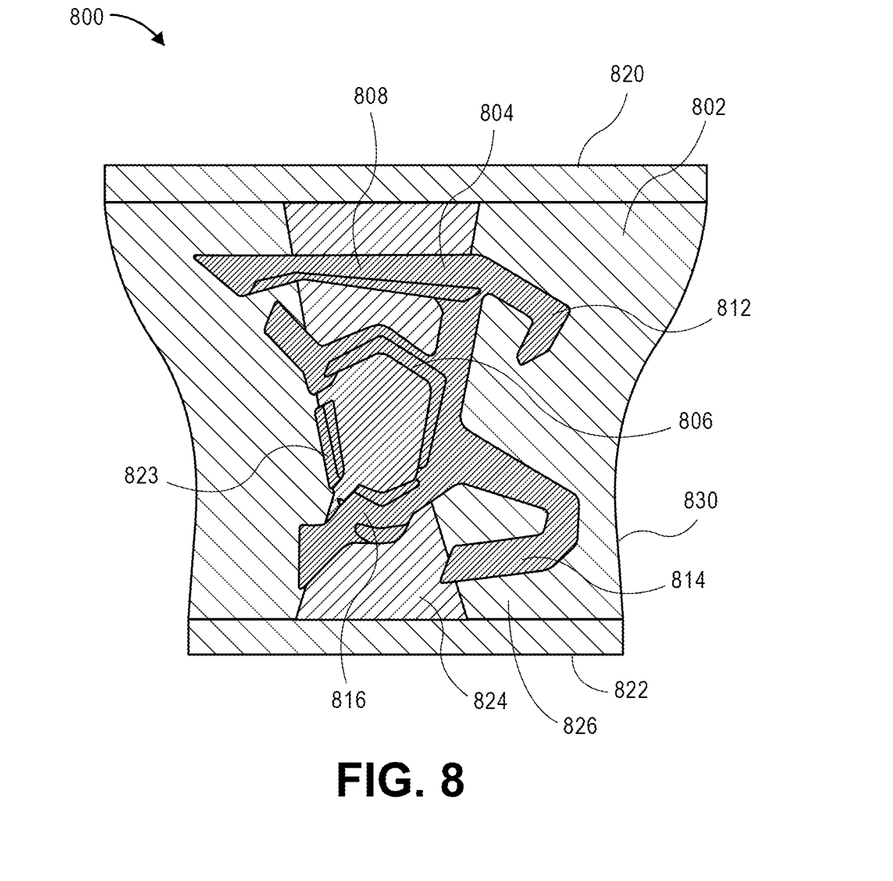
FIG. 8 is a plan view of the outer surface of yet another example of a support brace configured in accordance with an embodiment, being adapted to be worn on the knee, and shown cut open along a seam and laid flat.

FIG. 8 is a plan view of the outer surface of yet another example of a support brace 800 configured in accordance with an embodiment, being adapted to be worn on the knee, and shown cut open along a seam 830 and laid flat. In some embodiments, the brace 800 can be adapted to support an injured or otherwise painful knee, for example, to offload the knee joint and reduce pain from osteoarthritis. The brace 800 includes a flexible fabric base 802 having a proximal region 820 adapted to be positioned around the lower thigh, and a distal region 822 adapted to encircle the wearer's upper calf. The brace 800 also includes an elastomeric member 804. The elastomeric member 804 includes a curvilinear portion 806 configured to extend around the lateral side of the patella when the brace 800 is worn. As illustrated in FIG. 8, the curvilinear portion 806 is continuous along the length of the knee joint on the lateral side of the patella. By such a configuration, the elastomeric member 804 can help to resist extension of the knee on the lateral side. In some embodiments, the elastomeric member 804 or portions thereof (e.g., the curvilinear portion 806) can extend through an arc of between about 180 and 320 degrees about the wearer's patella, or through any other suitable range of degrees. The elastomeric member 804 also includes a thigh portion 808 which is configured to extend generally horizontally around a portion of the wearer's thigh. The thigh portion 808 can be adapted to provide compression across the bone/tendon junctures above the knee joint. The elastomeric member 804 can also include one or more wing portions 812, 814 which extend from the curvilinear portion 806 and which are configured to reinforce the pressure applied by the curvilinear portion 806 to the lateral side of the patella. It can be seen in FIG. 8 that the curvilinear portion 806 is discontinuous about the medial side of the patella. Such a discontinuity can facilitate or promote extension of the knee on the medial side. The elastomeric member 804 can include an enlarged portion 816 disposed below the patella, so as to apply pressure to the patellar tendon. In some embodiments, the brace 100 can include an additional elastomeric member 823 on the medial side of the patella, spaced apart from the first elastomeric member 804. In some embodiments, the elastomeric member(s) 804 and/or 823 can include regions of varying thickness, to provide even more variability of compression at different locations around the arm and/or elbow.

In some embodiments, the fabric base 802 can include regions with different degrees of stretchiness (e.g., different types of knit; different moduli of elasticity), also facilitating the provision of different levels of compression to different regions about the arm and/or elbow. For example, as illustrated in FIG. 8, the fabric base 802 can include a first region 824 having a relatively low elastic modulus, and a second region 826 having a relatively higher level of compression.

The various embodiments of support braces and techniques described above thus provide a number of ways to provide variable compression to a joint or limb, in a low-profile and lightweight brace. Of course, it is to be understood that not necessarily all such objectives or advantages may be achieved in accordance with any particular embodiment using the systems described herein. Thus, for example, those skilled in the art will recognize that the systems may be developed in a manner that achieves or optimizes one advantage or group of advantages as taught herein without necessarily achieving other objectives or advantages as may be taught or suggested herein.

Further, although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In particular, while the present support brace has been described in the context of a particularly configured knee brace, the skilled artisan will appreciate, in view of the present disclosure, that certain advantages, features and aspects of the support brace may be realized in a variety of other applications, many of which have been noted above. For example, while particularly useful for knee brace applications, such as the illustrated knee brace application, the skilled artisan can readily adopt the principles and advantages described herein to a variety of other applications, including wrist braces, elbow braces, shoulder braces, and ankle braces, as well as to any type of compression garment, such as compression shirts, vests, sleeves, pants, shorts, or socks.

Additionally, it is contemplated that various aspects and features of the invention described can be practiced separately, combined together, or substituted for one another, and that a variety of combination and subcombinations of the features and aspects can be made and still fall within the scope of the invention. Thus, it is intended that the scope of the present invention herein disclosed should not be limited by the particular disclosed embodiments described above, but should be determined only by a fair reading of the claims that follow.

What is claimed is:

1. A knee brace comprising:
   a flexible fabric substrate configured to encircle the knee of a wearer and to extend above and below the wearer's knee;
   a first elastomeric member disposed on a first surface of the flexible fabric substrate, the elastomeric member being configured to reduce loads on the knee joint; and
   a second elastomeric member disposed entirely to one of a lateral or medial side of a patella of the wearer's knee and secured to a second surface of the flexible fabric substrate that is configured to face the wearer's knee in an opposite direction from the first surface, the second elastomeric member comprising:
   a first portion configured to extend substantially longitudinally along the lateral or medial side of the patella;
   a plurality of bars, each extending from a different respective position on the first portion that is proximal of the patella and each configured to extend laterally away from the patella, and
   an additional bar extending substantially diagonally and laterally away from the patella from a position on the first portion that is distal of the plurality of bars.

2. The knee brace of claim 1, wherein the first elastomeric member is configured to apply pressure non-uniformly about the wearer's patella.

3. The knee brace of claim 1, wherein the first elastomeric member is configured to apply a frontal plane force so as to decrease pressure in at least one of the medial and lateral knee compartments.

4. The knee brace of claim 1, wherein the first elastomeric member is disposed on the first surface of the flexible fabric substrate so as to extend through an arc of between 180 and 320 degrees about the wearer's patella.

5. The knee brace of claim 1, wherein at least a portion of the first elastomeric member extends laterally of the wearer's patella.

6. The knee brace of claim 1, further comprising a third elastomeric member disposed on the first surface of the flexible fabric substrate, the third elastomeric member being spaced apart from the first elastomeric member, the third elastomeric member being disposed medially of the wearer's patella.

7. The knee brace of claim 6, wherein the third elastomeric member has a dimpled surface.

8. The knee brace of claim 1, wherein the first elastomeric member comprises silicone.

9. The knee brace of claim 1, wherein the first elastomeric member has a thickness of between 0.3 mm and about 5 mm.

10. The knee brace of claim 1, wherein the flexible fabric substrate comprises a generally tubular sleeve.

11. The knee brace of claim 1, wherein the flexible fabric substrate comprises a wrap-around.

12. The knee brace of claim 1, wherein the flexible fabric substrate comprises at least a first region and a second region, the second region having a higher modulus of elasticity than the first region.

13. The knee brace of claim 1, wherein the first elastomeric member is joined to the flexible fabric substrate without adhesive.

14. A method of manufacturing a knee brace, the method comprising:
   providing a flexible fabric substrate configured to encircle the knee of a wearer and to extend above and below the wearer's knee;
   securing a first elastomeric member to a first surface of the flexible fabric substrate in a pattern selected to reduce loads on the knee joint; and
   securing a second elastomeric member to a second surface of the flexible fabric substrate that is configured to face the wearer's knee in an opposite direction from the first surface entirely to one of a lateral or medial side of a patella of the wearer's knee, the second elastomeric member comprising:

a first portion configured to extend substantially longitudinally along the lateral or medial side of the patella, a plurality of bars, each extending from a different respective position on the first portion that is proximal of the patella and each configured to extend laterally away from the patella, and an additional bar extending substantially diagonally and laterally away from the patella from a position on the first portion that is distal of the plurality of bars.

15. The method of claim 14, wherein the first elastomeric member is applied by an injection molding process.

16. The method of claim 14, wherein the first elastomeric member is applied to a thickness of between 0.3 mm and 5 mm.

17. The method of claim 14, wherein the first elastomeric member is applied to the first surface of the flexible fabric substrate so as to extend through an arc of between 180 and 320 degrees about the wearer's patella.

18. The method of claim 14, further comprising applying a third elastomeric member to the first surface of the flexible fabric substrate, the third elastomeric member being spaced apart from the first elastomeric member such that the third elastomeric member is disposed medially of the wearer's patella.

19. The method of claim 14, wherein the first elastomeric member is secured to the flexible fabric substrate without adhesive.

20. The method of claim 14, wherein at least a portion of the first elastomeric member extends laterally of the wearer's patella.

* * * * *